(12) United States Patent
Chandran et al.

(10) Patent No.: US 12,059,274 B2
(45) Date of Patent: Aug. 13, 2024

(54) SYSTEM FOR DISPLAYING OXYGEN STATE INDICATIONS

(71) Applicant: Masimo Corporation, Irvine, CA (US)

(72) Inventors: Prashanth Rengaswamy Chandran, Irvine, CA (US); Anand Sampath, Irvine, CA (US); Keith Ward Indorf, Lake Elsinore, CA (US); Sebastian T. Frey, Laguna Niguel, CA (US); Bilal Muhsin, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 513 days.

(21) Appl. No.: 17/218,746

(22) Filed: Mar. 31, 2021

(65) Prior Publication Data

US 2021/0212640 A1 Jul. 15, 2021

Related U.S. Application Data

(63) Continuation of application No. 16/175,474, filed on Oct. 30, 2018, now Pat. No. 10,987,066.

(60) Provisional application No. 62/579,575, filed on Oct. 31, 2017.

(51) Int. Cl.
*A61B 5/1455* (2006.01)
*A61B 5/00* (2006.01)

(52) U.S. Cl.
CPC .......... *A61B 5/7445* (2013.01); *A61B 5/0082* (2013.01); *A61B 5/14551* (2013.01); *A61B 5/14552* (2013.01); *A61B 5/6826* (2013.01); *A61B 5/746* (2013.01); *A61B 5/7435* (2013.01); *A61M 2205/3306* (2013.01); *A61M 2230/205* (2013.01)

(58) Field of Classification Search
CPC .............. A61B 5/1455; A61B 5/14551; A61B 5/14552; A61B 5/7275; A61B 5/742
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |

(Continued)

FOREIGN PATENT DOCUMENTS

WO WO 2019/089655 5/2019

OTHER PUBLICATIONS

IconBros, https://www.iconbros.com/icons/ib-mi-f-map, retrieved Nov. 3, 2020, Medical Item Collection, Map Icon Image, pp. 1.

(Continued)

*Primary Examiner* — Eric F Winakur
(74) *Attorney, Agent, or Firm* — Knobbe, Martens, Olson & Bear, LLP

(57) ABSTRACT

A patient monitoring system can have a display screen or portion thereof with graphic user interface for displaying indications of a patient's oxygen state. The indications can include the patient's $SpO_2$, dissolved oxygen index, and/or an increasing or decreasing trend of dissolved oxygen index. The displays of oxygen state indications can be compact, and/or able to provide direct visual information to a user of various aspects of the patient's oxygen state. The display elements can be used to represent any other physiological parameters.

4 Claims, 12 Drawing Sheets

(56) References Cited

U.S. PATENT DOCUMENTS

| | | |
|---|---|---|
| 5,341,805 A | 8/1994 | Stavridi et al. |
| 5,355,880 A | 10/1994 | Thomas et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,743,172 B1 | 6/2004 | Blike |

(56) References Cited

U.S. PATENT DOCUMENTS

| | | |
|---|---|---|
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |

(56) References Cited

U.S. PATENT DOCUMENTS

| | | |
|---|---|---|
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| D667,842 S | 9/2012 | Ouilhet |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| D689,091 S | 9/2013 | Impas et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| D693,365 S | 11/2013 | Gardner et al. |
| 8,577,431 B2 | 11/2013 | Lamego et al. |
| 8,577,433 B2 | 11/2013 | McKenna |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |

(56) References Cited

U.S. PATENT DOCUMENTS

| | | |
|---|---|---|
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,046 S | 12/2015 | Shin et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| D753,716 S | 4/2016 | Torres et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| D763,317 S | 8/2016 | Kim et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| D772,931 S | 11/2016 | Vulk et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| D775,663 S | 1/2017 | Akana et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |

(56) References Cited

U.S. PATENT DOCUMENTS

| | | |
|---|---|---|
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D819,660 S | 6/2018 | Cabrera, Jr. et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D844,642 S | 4/2019 | Cabrera, Jr. et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,402,650 B1 | 9/2019 | Suiter et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| D870,773 S | 12/2019 | Marrufo |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |

(56) References Cited

U.S. PATENT DOCUMENTS

| | | |
|---|---|---|
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D989,112 S | 6/2023 | Muhsin et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0074321 A1 | 4/2006 | Kouchi et al. |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0331639 A1 | 12/2010 | O'Reilly |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |

(56) References Cited

U.S. PATENT DOCUMENTS

| | | |
|---|---|---|
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0000362 A1 | 1/2016 | Diab et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0119210 A1 | 4/2016 | Koehler et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |

(56) References Cited

U.S. PATENT DOCUMENTS

| | | |
|---|---|---|
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |

OTHER PUBLICATIONS

International Search Report and Written Opinion in corresponding International Patent Application No. PCT/US2018/058294, mailed Feb. 12, 2019, in 12 pages.

SYSTEM FOR DISPLAYING OXYGEN STATE INDICATIONS

INCORPORATION BY REFERENCE TO ANY PRIORITY APPLICATIONS

The present application is a continuation of U.S. patent application Ser. No. 16/175,474, filed Oct. 30, 2018, entitled "SYSTEM FOR DISPLAYING OXYGEN STATE INDICATIONS," which claims priority benefit under 35 U.S.C. § 119(e) to U.S. Provisional Application No. 62/579,575, filed Oct. 31, 2017, titled "SYSTEM FOR DISPLAYING OXYGEN STATE INDICATIONS," incorporated herein by reference in its entirety.

Any and all applications for which a foreign or domestic priority claim is identified in the Application Data Sheet as filed with the present application are hereby incorporated by reference under 37 CFR 1.57.

FIELD

The present invention relates to the field of noninvasive oxygen delivery measurement using optical based sensors, and in particular, to displaying indication(s) of a patient's oxygen state.

BACKGROUND

The measurement of oxygen delivery to the body and the corresponding oxygen consumption by the body's organs and tissues is vitally important to medical practitioners in the diagnosis and treatment of various medical conditions. Oxygen delivery is useful, for example, during certain medical procedures, where artificially providing additional oxygen to the patient's blood stream may become necessary. Patients may need supplemental oxygen in surgery, conscious sedation, or the intensive care unit. For example, during an intubation procedure, the patient will stop breathing while the procedure is performed. The patient is typically provided with oxygen before the intubation procedure. However, because the patient stops breathing during an intubation procedure, the patient's blood oxygen saturation level can fall. The medical practitioner must ensure that the patient has sufficient reserves of oxygen in the system before intubation so that suffocation is avoided during the intubation procedure. At the same time, providing oxygen at a high pressure to a patient can have its own negative effects in some patients, some of which include damages to the patient's lungs, and in particular, to the alveoli structures in the lungs. In some patients, for example neonates, even oxygen levels on the high end of a normal oxygenation range can cause blindness.

SUMMARY

When oxygen molecules come into contact with blood, the majority of the oxygen molecules are bound to the hemoglobin in red-blood cells and a small portion is dissolved directly in the blood plasma. The current standard of care is to measure oxygen delivery through the use of a pulse oximeter. Pulse oximeters noninvasively measure and display oxygen saturation ($SpO_2$), which is the percentage of the patient's hemoglobin bound to oxygen molecules.

Another possible indicator of oxygen delivery is the partial pressure of oxygen ($PaO_2$) in the arterial blood. However, there are currently no reliable ways to measure arterial $PaO_2$ noninvasively. Invasive $PaO_2$ measurements require a blood gas analysis. The analysis may be needed intermittently during a surgical procedure and can interrupt and/or delay the surgical procedure. The analysis may require expensive sensors. Invasive $PaO_2$ measurements may also carry serious side effects that can harm the health of a patient.

One of the challenges of commercially available physiological monitors that provide $SpO_2$ readings is that the relationship between a patient's $PaO_2$ and $SpO_2$ is not linear. Specifically, $SpO_2$ measured by pulse oximetry can be reported as high as about 98% even when $PaO_2$ is as low as about 70 mmHg. A patient can be in a hypoxic state when the patient's $PaO_2$ falls below about 80 mmHg. Therefore, $SpO_2$ may not provide advance warning of falling arterial oxygenation until the patient's $PaO_2$ is already in the hypoxia range, which may not be adequate for providing advance warning of impending hypoxia. In an effort to prevent hypoxia, clinicians can provide supplemental oxygen to maintain $SpO_2$ at greater than about 98% during surgery to provide a "safety cushion" of oxygenation in the event of unexpected changes in oxygen delivery. However, the "safety cushion" can result in significant hyperoxia. When the $SpO_2$ level reaches or is close to 100%, the $PaO_2$ level can continue to rise if oxygen continues to be dissolved in the plasma. $SpO_2$ is not able to inform clinicians or any other users of an increasing amount of oxygen dissolved in the patient's blood beyond 100% $SpO_2$, when substantially all the hemoglobin has been fully saturated with oxygen modules. Hyperoxia have its own negative effects, including those described above. Therefore, providing information of the patient's hypersaturation condition can be helpful in allowing the clinician to stop delivery of supplemental oxygen temporarily and resume oxygen delivery when it is safe to do so.

Pulse oximeters according to the present disclosure can provide an index indicative of oxygen dissolved in the blood (hereinafter referred to as the "dissolved oxygen index" or the "index"). Example methods of determining such an index are described in U.S. Pat. No. 9,131,881, titled "HYPERSATURATION INDEX" and issued Sep. 15, 2015, the entirety of which is incorporated by reference herein. An example of the index is the Oxygen Reserve Index™ (ORi™). The index can add to or supplement information from $SpO_2$, and/or invasive $PaO_2$ measurements using other equipment. The index is configured to provide information about oxygen dissolved in a patient's blood, which can indicate the patient's oxygenation in a moderate hyperoxic range. The moderate hyperoxic range can be, for example, when the patient's $PaO_2$ is between about 100 mmHg to about 200 mmHg. The pulse oximeter can be a standalone device or docked to a multi-parameter medical hub. The index can be displayed on a display screen of the standalone device and/or on a display screen of the medical hub.

The present disclosure provides various displays of indications of a patient's oxygen state including a patient's blood oxygenation state, such as the index, a patient's impending hypoxia and/or hyperoxia, and/or $SpO_2$. For example, the displays can inform a user of the patient's index when $SpO_2$ is high, such as greater than about 98%. Displaying various oxygen state indications on the same screen can provide a more comprehensive picture of the patient's oxygen state than displaying only $SpO_2$. The displays can be useful for patients who are on supplemental oxygen therapy, a ventilator or closed-loop positive pressure delivery device, or for any other medical applications where a patient's oxygen state needs to be monitored.

Another one of the challenges of commercially available physiological monitors is the limited display screen size, when patient monitors continue to expand in the number and type of monitored parameters made available to a user for review. Although a user is able to conveniently access a large amount of a patient's data from a single display screen, the display can become cluttered with the large number of parameters. It can also be challenging for the user to quickly and accurately understand the various oxygen state parameters shown on the display screen, among other physiological parameters, so as to make decisions about how to care for the patient.

The displays of oxygen state indications according to the present disclosure can be compact, and/or able to provide direct visual information of various aspects of the patient's oxygen state to a user reading the display screen. Examples of the aspects of the patient's oxygen state can include graphs, symbols, numerical indications, and/or a combination thereof, of $SpO_2$, the index, such as ORi™, and/or an increasing or decreasing trend of the index.

A noninvasive patient monitoring system for providing an indication of a patient's oxygen state system for providing an indication of a patient's oxygen state can comprise one or more sensors for outputting signals in response to a plurality of a patient's physiological parameters; one or more signal processors configured to receive the signals and calculate a first indicator responsive to a percentage of hemoglobin molecules bound to oxygen, a second indicator responsive to a quantity of oxygen dissolved in the patient's blood and not bound to any hemoglobin molecule, the second indicator providing different information to a caregiver than the first indicator, and a third indicator responsive to an increasing or decreasing trend of the second indicator; and a display responsive to output of the one or more signal processors to display the first, second, and third indicators. The first indicator can comprise the patient's oxygen saturation. The first indicator can be displayed as a graph and/or a numerical value. The second indicator can comprise a noninvasive index of dissolved oxygen in blood of the patient. The second indicator can be displayed as a plurality of shapes, the number of shapes being displayed corresponding to the patient's noninvasive index of dissolved oxygen in the blood. The shape can be a rectangle, a circle, a triangle, or a diamond. No shape may be displayed when the first indicator is below about 98%. The third indicator can further comprise a rate of increase or decrease of the patient's noninvasive index of dissolved oxygen in the blood. The third indicator can be displayed as an arrow pointing at an angle, a direction of the arrow corresponding to the increasing or decreasing trend of the patient's noninvasive index of dissolved oxygen in the blood and a magnitude of the angle corresponding to the rate of increase or decrease of the patient's noninvasive index of dissolved oxygen in the blood. The arrow can be displayed as pointing generally horizontally when the first indicator is below about 98%. The second indicator can be displayed as a shape that is empty, partially filled, or fully filled, the amount of filling corresponding to the patient's noninvasive index of dissolved oxygen in the blood. The shape can be empty when the first indicator is below about 98%. The shape can comprise a circle, a triangle, a rectangle, or a diamond. The third indicator can be displayed as a pointer placed at an angle, the pointer coupled with the shape to form a dial, a clock direction of the pointer corresponding to the increasing or decreasing trend of the patient's noninvasive index of dissolved oxygen in the blood and/or the rate of increase or decrease of the patient's noninvasive index of dissolved oxygen in the blood. The dial can display about 3 o'clock when the first indicator is below about 98%. The one or more sensors can comprise an optical sensor having at least one light emitter emitting light of a plurality of wavelengths into the body of the patient and a light detector detecting the light after attenuation of the body, wherein the attenuation can be responsive to oxygenation of the patient's blood. The first indicator can be determined based at least in part on the detected light. The second indicator can be determined based at least in part on the detected light. The third indicator can be determined based at least in part on the detected light.

A noninvasive patient monitoring system for providing an indication of a patient's oxygen state system for providing an indication of a patient's oxygen state can comprise at least one light emitter emitting light of a plurality of wavelengths into the body of the patient; a light detector detecting the light after attenuation of the body, wherein the attenuation can be responsive to oxygenation of the patient's blood, and outputting one or more signals from the light detector, the one or more signals responsive to said attenuation; one or more signal processors configured to process the one or more signals to electronically calculate a first indicator responsive to a quantity of oxygen dissolved in the patient's blood and not bound to any hemoglobin molecule, and a second indicator responsive to an increasing or decreasing trend of the first indicator; and a display responsive to output of the one or more signal processors to display the first and second indicators. The one or more signal processors can be further configured to calculate a third indicator responsive to a percentage of hemoglobin molecules bound to oxygen, the third indicator providing different information to a caregiver than the first or second indicator, and the display can be configured to display the third indicator. The third indicator can comprise the patient's oxygen saturation. The third indicator can be displayed as a graph and/or a numerical value. The first indicator can comprise the patient's noninvasive index of dissolved oxygen in the blood. The first indicator can be displayed as a plurality of shapes, the number of shapes being displayed corresponding to the patient's noninvasive index of dissolved oxygen in the blood. The shape can be a rectangle, a circle, a triangle, or a diamond. No shape may be displayed when the patient's oxygen saturation is below about 98%. The second indicator can further comprise a rate of increase or decrease of the patient's noninvasive index of dissolved oxygen in the blood. The second indicator can be displayed as an arrow at an angle, a direction of the arrow corresponding to the increasing or decreasing trend of the patient's noninvasive index of dissolved oxygen in the blood and a magnitude of the angle corresponding to the rate of increase or decrease of the patient's noninvasive index of dissolved oxygen in the blood. The arrow can be displayed as pointing generally horizontally when the first indicator is below about 98%. The first indicator can be displayed as a shape that is empty, partially filled, or fully filled, the amount of filling corresponding to the patient's noninvasive index of dissolved oxygen in the blood. The shape can be empty when the patient's oxygen saturation is below about 98%. The shape can comprise a circle, a triangle, a rectangle, or a diamond. The second indicator can be displayed as a pointer directed at an angle, the pointer coupled with the shape to form a dial, a clock direction of the pointer corresponding to an increasing or decreasing trend of the patient's noninvasive index of dissolved oxygen in the blood and/or the rate of increase or decrease of the patient's noninvasive index of dissolved oxygen in the blood. The dial can display about three o'clock when the first indicator is below about 98%.

A noninvasive patient monitoring system for providing an indication of a physiological parameter can comprise one or more sensors for outputting signals in response to a patient's physiological conditions; one or more signal processors configured to receive the signals and calculate a first indicator responsive to a magnitude of a physiological parameter, and a second indicator responsive to an increase or decrease of the physiological parameter; and a display responsive to output of the one or more signal processors to display the first and second indications. The second indicator can be further responsive to a rate of change of the physiological parameter. The first indicator can comprise a plurality of shapes, the number of shapes displayed corresponding to the magnitude of the physiological parameter. No shape may be displayed when the physiological parameter is zero or cannot be calculated. The shape can comprise a rectangle, a circle, a triangle, or a diamond. The second indicator can comprises an arrow. An angle of the arrow can correspond to the rate of change of the physiological parameter. The first indicator can comprise a shape that is empty, partially filled, or fully filled, the amount of filling corresponding to the magnitude of the physiological parameter. The shape can be empty when the physiological parameter is zero or cannot be calculated. The shape can comprise a circle, a triangle, a rectangle, or a diamond. The second indicator can comprise a pointer, the pointer coupled with the shape to form a dial, a clock direction of the pointer corresponding to the increase or decrease of the physiological parameter and/or the rate of change of the physiological parameter. The physiological parameter can be a patient's noninvasive index of dissolved oxygen in blood.

A noninvasive patient monitoring system for providing an indication of a patient's oxygen state system for providing an indication of a patient's oxygen state can comprise at least one light emitter emitting light of a plurality of wavelengths into the body of the patient, a light detector detecting the light after attenuation of the body, wherein the attenuation is responsive to oxygenation of the patient's blood, and outputting one or more signals from the light detector, the one or more signals responsive to said attenuation, and one or more signal processors configured to process the one or more signals to electronically calculate an indicator responsive to a quantity of oxygen dissolved in the patient's blood and not bound to any hemoglobin molecule and output an alert of the first indicator plateauing at a maximum value in response to an increase in oxygen supply to the patient. The system can further comprise a display screen responsive to output of the one or more signal processors to display the first indicator. The display can be further configured to display the alert. The system can also be configured to output the alert in an audio form. The first indicator can comprise a plurality of shapes, the number of shapes displayed corresponding to the magnitude of the quantity of oxygen dissolved in the patient's blood and not bound to any hemoglobin molecule. The first indicator can further comprise an indication of an increasing or decreasing trend of the magnitude. The increase in oxygen supply to the patient can be determined by monitoring the patient's $FiO_2$.

BRIEF DESCRIPTION OF THE DRAWINGS

The drawings and following associated descriptions are provided to illustrate embodiments of the present disclosure and do not limit the scope of the claims. Corresponding numerals indicate corresponding parts, and the leading digit of each numbered item indicates the first figure in which an item is found.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit the scope of the disclosure herein, which is instead defined by the claims following this description.

Figure 1A:
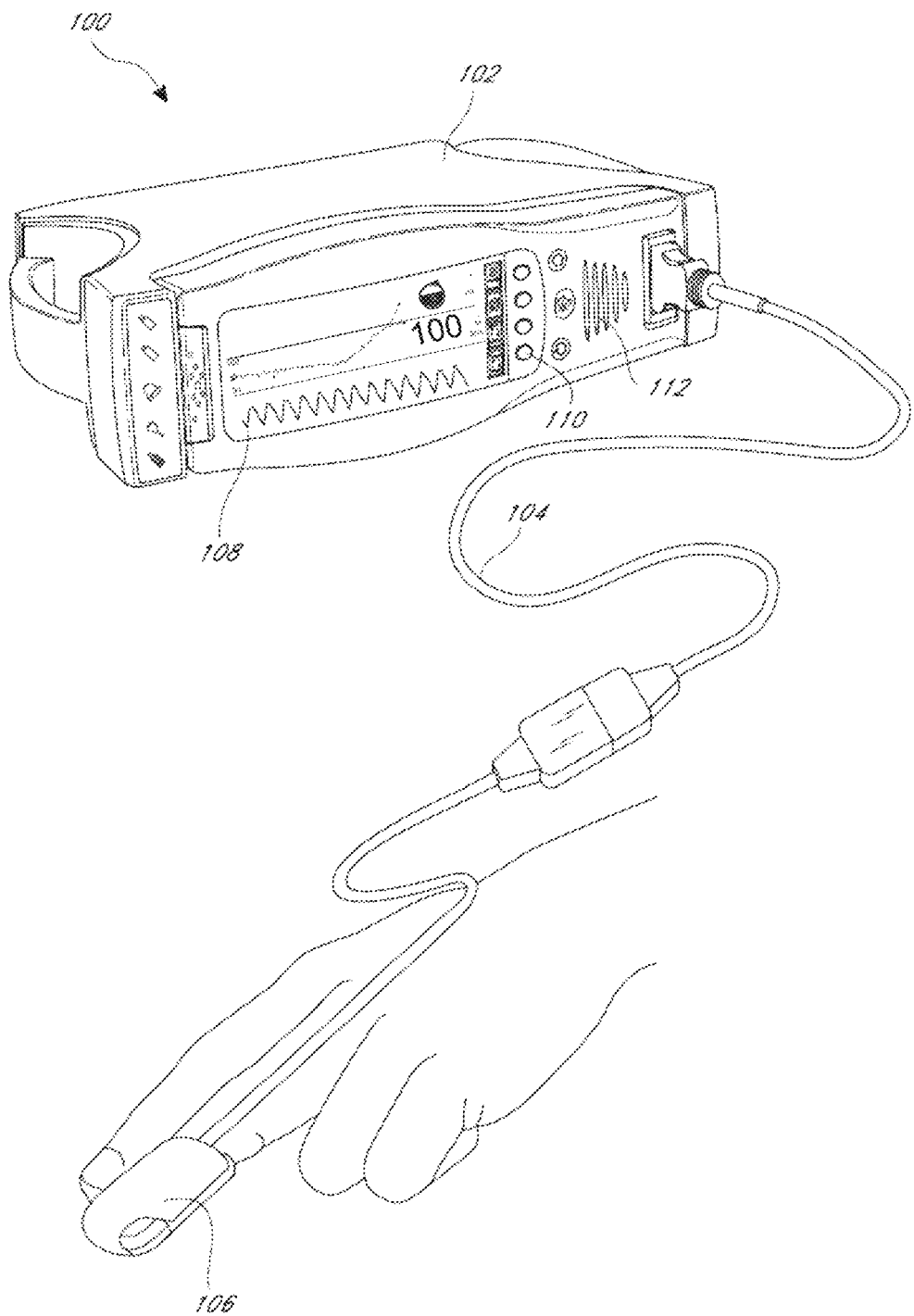
FIG. 1A illustrates a perspective view of a patient monitoring system having a user-interface displaying a patient's physiological parameter(s).

FIG. 1A illustrates an example patient monitoring system 100. The patient monitoring system 100 can include a patient monitor 102 attached to a sensor 106 by a cable 104. The sensor 106 can be an optical based sensor including one or more optical emitters and one or more optical detectors. In addition to the sensor 106 as illustrated in FIG. 1A, other types of sensor(s) that can be coupled to the patient monitor 102. The sensor 106 can monitor various physiological data of a patient and send signals indicative of the parameters to the patient monitor 102 for processing. For example, the one or more optical detectors can detect a plurality of wavelengths from the emitters after attenuation by the patient's body tissue. The patient monitoring system 100 can monitor $SpO_2$, indications of hypersaturation, perfusion index (PI), pulse rate (PR), hemoglobin count, and/or other parameters based at least in part on the signals received from the sensor(s).

The patient monitor 102 can include a display 108, control button(s) 110, and a speaker 112 for audible alerts. The display 108 can include a graphic user-interface, which can be capable of displaying readings of various monitored patient parameters. The readings can include numerical readouts, graphical readouts, animations, and/or the like. The display 108 can include a liquid crystal display (LCD), a cathode ray tube (CRT), a plasma screen, a Light Emitting Diode (LED) screen, Organic Light Emitting Diode (OLED) screen, or any other suitable display.

Figure 1B:
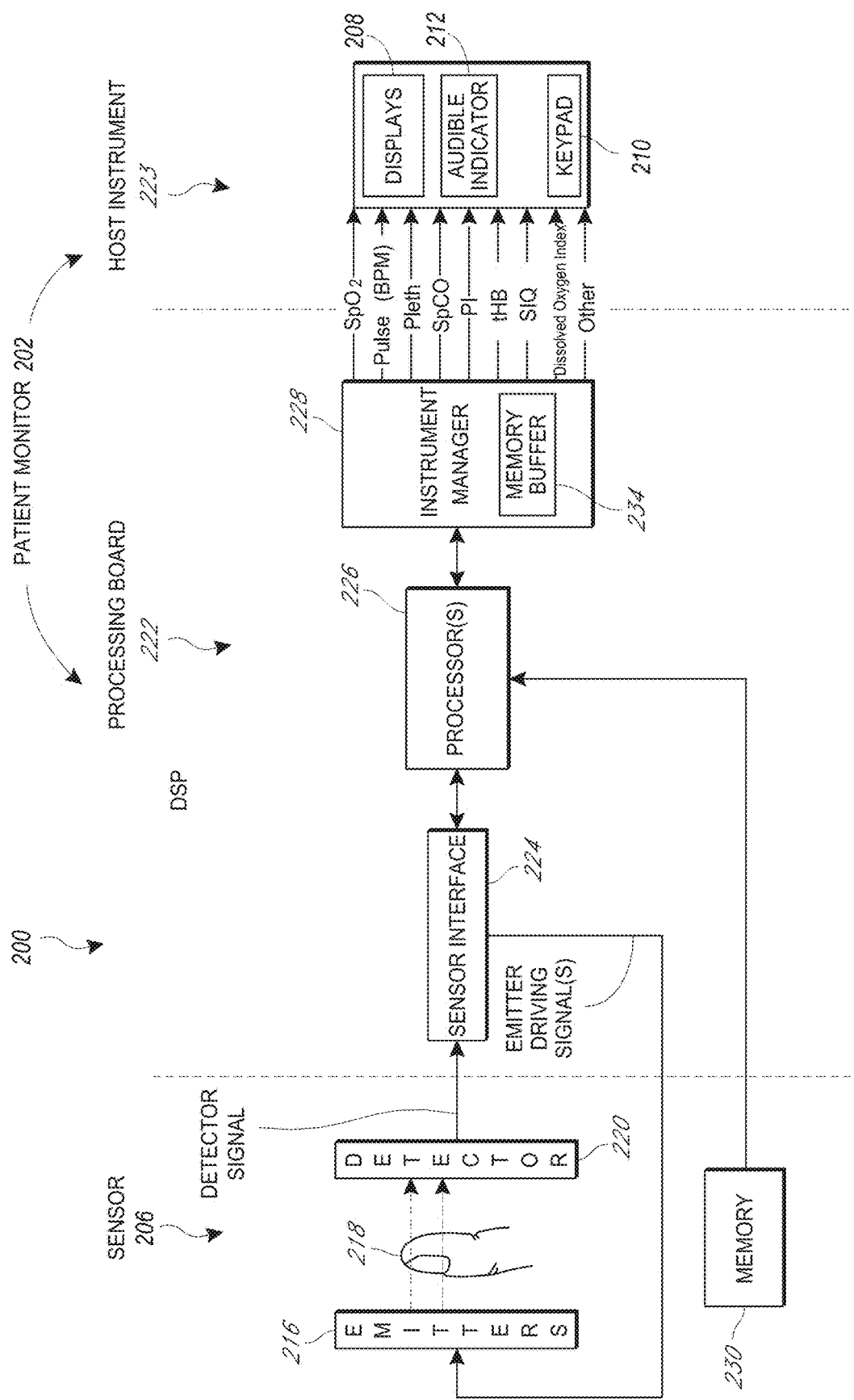
FIG. 1B illustrates a block drawing of an example patient monitoring system.

FIG. 1B illustrates details of a patient monitoring system 200 in a schematic form. A sensor 206 can include energy emitters 216 and one or more detectors 220. The energy emitters can be located on one side of a patient monitoring site 218. The one or more detectors 220 can be located generally opposite the energy emitters 216. The patient monitoring site 218 can be a patient's finger as shown in FIG. 1B. The patient monitoring site 218 can also be the patient's toe, ear lobe, and/or the like. The energy emitters 216 can include LEDs or any other suitable optical emitters. The energy emitters 216 can emit various wavelengths of electromagnetic energy through the flesh of a patient at the monitoring site 218. The emitted wavelengths can be in the red and infrared ranges. The electromagnetic energy signals can be attenuated as the signals travel through the flesh of the patient at the monitoring site 218. The detector(s) 220 can detect the attenuated energy and send representative signals in response to the detected energy to the patient monitor 202 for processing. The patient monitor 202 can include a processing board 222 and a host instrument 223. The processing board 222 can include a sensor interface 224, signal processor(s) 226, and an instrument manager 228.

The host instrument can include one or more displays 208, a keypad 210, a speaker 212 for audio messages, and a wireless signal broadcaster 234. The keypad 210 can comprise a full keyboard, a track wheel, control buttons, and the like. The patient monitor 202 can also include buttons, switches, toggles, check boxes, and the like implemented in software and actuated by a mouse, trackball, touch screen, joystick, or other input device.

The sensor interface 224 can receive the signals from the sensor detector(s) 220 and pass the signals to the processor (s) 226 for processing into representations of physiological parameters. The representations of physiological parameters can be passed to the instrument manager 228. The instrument manager 228 can further process the parameters for display by the host instrument 223. The processor(s) 226 can also communicate with a memory 230 located on the sensor 106. The memory 230 can contain information related to properties of the sensor 106 that can be used during processing of the signals. A non-limiting example of information stored in the memory 230 can be the wavelengths emitted by the emitter 216. The various elements of the processing board 222 described above can provide processing of the detected signals. Tracking medical signals can be difficult because the signals may include various anomalies that do not reflect an actual changing patient parameter. The processing board 222 can apply filters and/or algorithms to detect truly changing conditions from limited duration anomalies. The host instrument 223 can display one or more physiological parameters according to instructions from the instrument manager 228. Additionally, the physiological parameter measurements can be sent to a remote server (such as a cloud server) or to a remote monitoring device, such as a cell phone, tablet, or laptop. The patient monitoring system can include a data transmitter, such as a wireless transmitter or transceiver, for electrically communicating with the remote server or remote monitoring device.

Figure 2A:
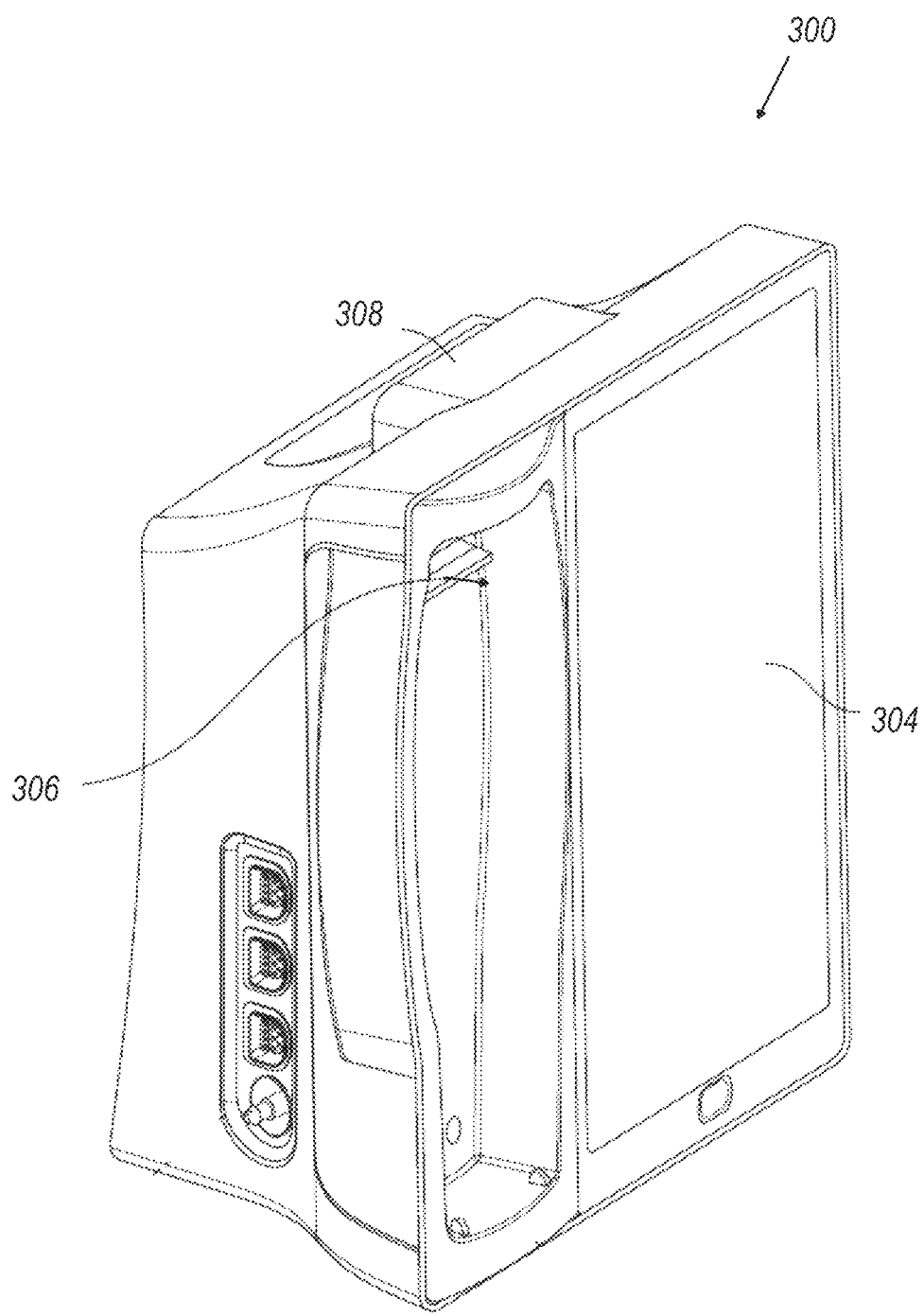
FIG. 2A illustrates a perspective view of an example medical monitoring hub having a user-interface displaying a patient's physiological parameter(s).
Figure 2B:
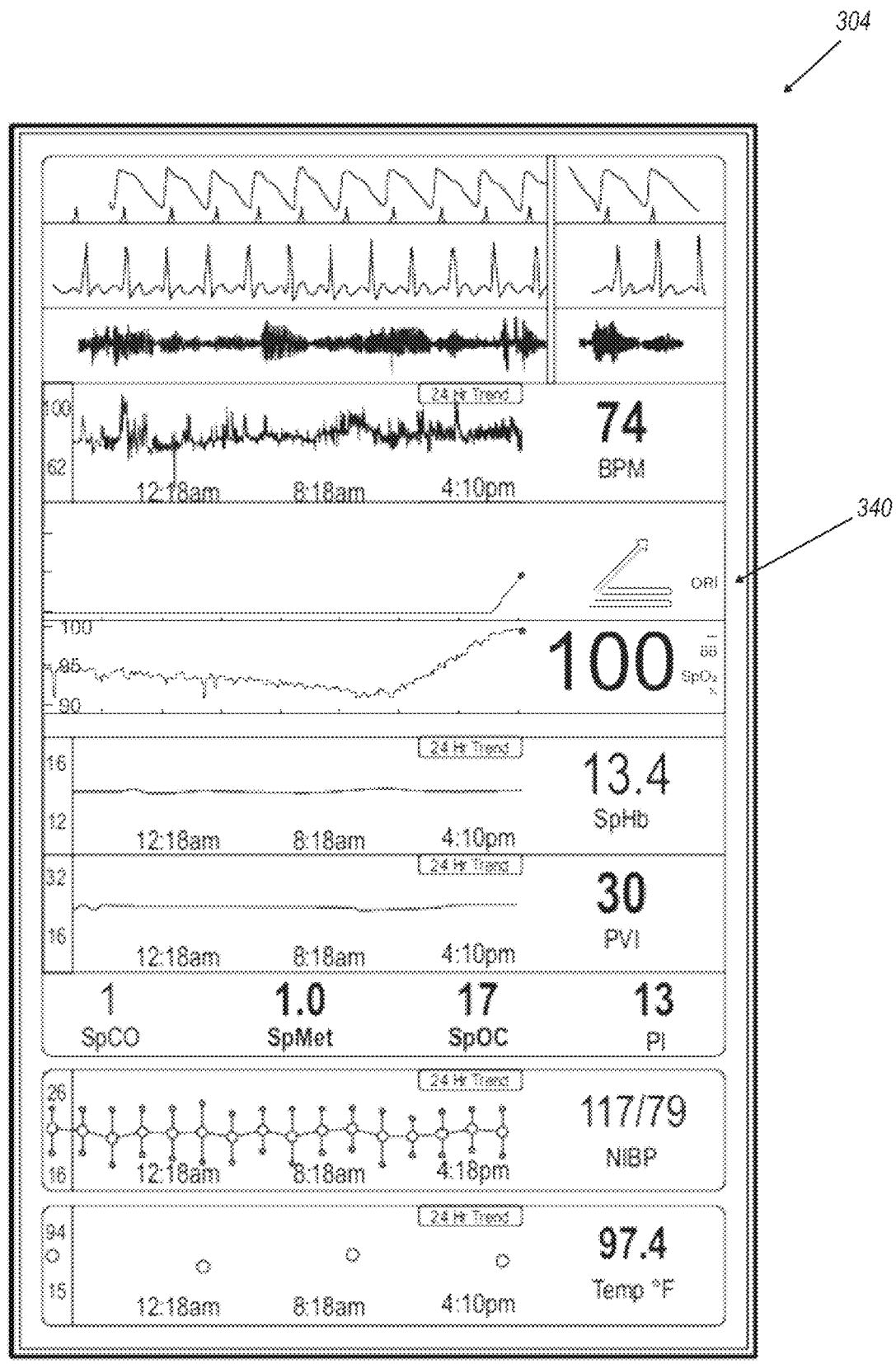
FIG. 2B illustrates an example display screen of a medical monitoring hub.

FIG. 2A illustrates a perspective view of an exemplary medical monitoring hub 300. The hub 300 can include a display 304 and a docking station 306. The docking station can be configured to mechanically and electrically mate with a portable patient monitor, such as the patient monitor 102, 202 in FIGS. 1A-1B. The display 304 can present various measurement and/or treatment data in numerical, graphical, waveform, or other display indicia 310, such as illustrated in FIG. 2B.

The display 304 can occupy a portion of a front face of the housing 308, or comprise a tablet or tabletop horizontal configuration, a laptop-like configuration or the like. Display information and data can optionally be communicated to a table computer, smartphone, television, or any other display system. The hub 300 can receive data from a patient monitor while docked or undocked from the hub.

Examples of patient monitors that can be docked to the hub 300 can include oximeters or co-oximeters, which are can provide measurement data for a large number of physiological parameters derived from signals output from optical and/or acoustic sensors, electrodes, and/or the like. The physiological parameters can include oxygen saturation, a dissolved oxygen index (such as, for example, ORi™), carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, or combinations of thereof. The hub 300 can also optionally output data sufficient to accomplish closed-loop drug administration in combination with infusion pumps or the like. Additional details of the medical hub 300 are described in U.S. application Ser. No. 14/512,237, filed Oct. 10, 2014 and titled "SYSTEM FOR DISPLAYING MEDICAL MONITORING DATA," the entirety of which is incorporated herein by reference and should be considered a part of the specification.

Figure 3:
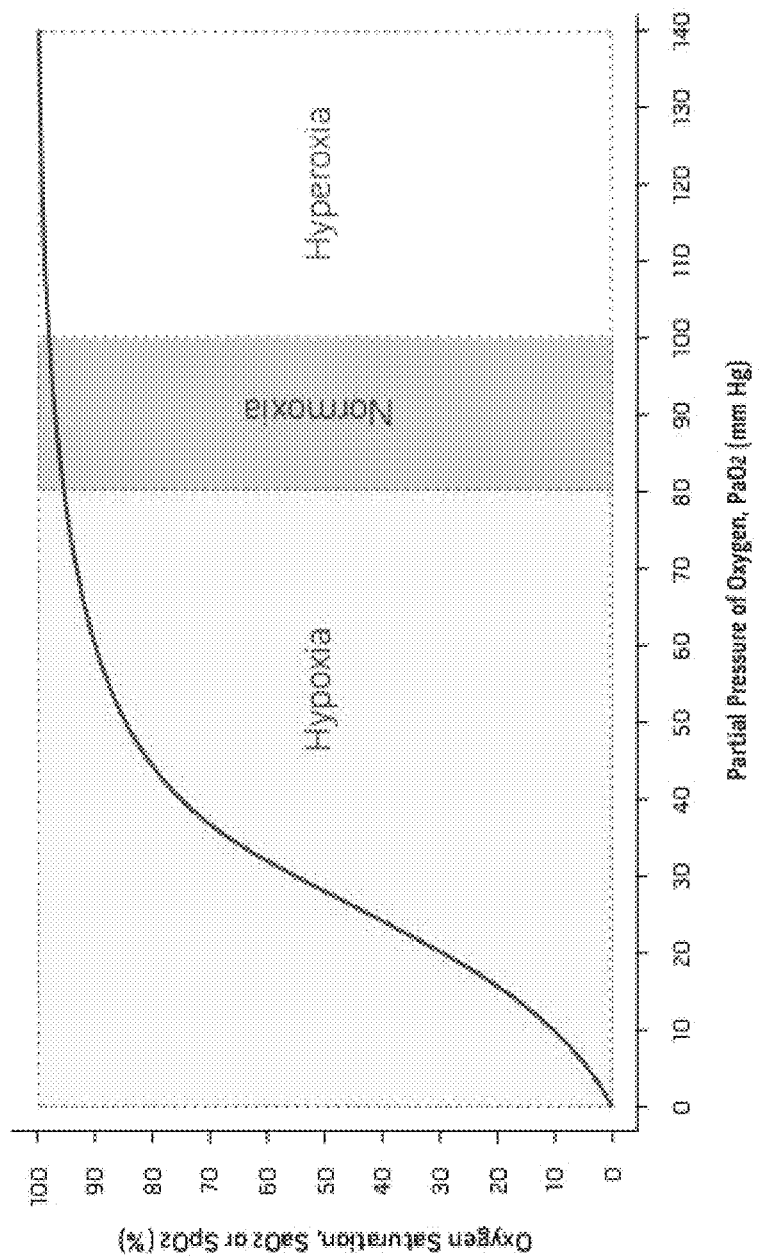
FIG. 3 illustrates an example oxygen dissociation curve of a human patient.

FIG. 3 illustrates the nonlinear relationship between the oxygen saturation and the partial pressure of oxygen in blood. The graph in FIG. 3 illustrates how oxygen saturation in the blood, $SpO_2$, or in the arterial blood, $SaO_2$, changes with respect to the $PaO_2$ in the blood. In this disclosure, $SpO_2$ is used interchangeably with $SaO_2$. A patient can be in a hypoxic state (less than normal oxygenation) when the patient's $PaO_2$ is below about 80 mmHg. A patient can be in a normoxic state (normal oxygenation) when the patient's $PaO_2$ is between about 80 mmHg and about 100 mmHg. A patient can be in a hyperoxic state (higher than normal oxygenation) when the patient's $PaO_2$ exceeds about 100 mmHg. A patient can be in a moderate hyperoxic state when the patient's $PaO_2$ is between about 100 mmHg to about 200 mmHg.

As shown in FIG. 3, $SpO_2$ initially increases as $PaO_2$ in the blood increases. After the $SpO_2$ and/or $SaO_2$ level(s) reach about 100%, the $PaO_2$ level continues to rise, but the $SpO_2$ and/or $SaO_2$ level off. As a result, $SpO_2$ measured using pulse oximetry can allow a user to monitor a patient's arterial blood oxygenation in hypoxia and/or normoxia, but not in hyperoxia. In addition, the increase in $SpO_2$ is small when a patient is in the normoxic and hyperoxic states. The $SpO_2$ reading can exceed about 95%, and be as high as about 98%, when $PaO_2$ is as low as about 70 mmHg. Therefore, when $PaO_2$ is transiting from the normoxic range to the hyperoxic range, $SpO_2$ reading may not be sensitive enough to provide advance warning of impending hypoxia. The patient can quickly be in hypoxia after the patient's dissolved oxygen is depleted without warning to the user. It can be too late when the user realizes that the patient is in hypoxia. The patient may continue to have insufficient oxygen until an increased delivery of oxygen brings the patient's oxygenation back to the normoxic range.

As described above, clinicians can deliver oxygen to maintain the patient's $SpO_2$ at greater than about 98% during surgery to have some reserve of oxygen in the blood in the event of unexpected changes in oxygen delivery. Such changes can occur due to, for example, cardiac depression, rapid hemorrhage, and/or interrupted ventilation. However, too much excess oxygen above about 98% $SpO_2$ can result in significant hyperoxia, which cannot be known from $SpO_2$ readings.

The patient monitoring system can be configured to measure the patient's hypersaturation conditions, that is, when the patient is in hyperoxia, in addition to monitoring $SpO_2$ and/or invasive $PaO_2$ measurements. The patient monitoring system can also be configured to inform a user of the patient's impending hypoxia. The patient monitoring system can be the patient monitor 102, 202 of FIGS. 1A and 1, the patient monitor configured to be used with the medical hub 300 of FIGS. 2A and 2B, or any other patient monitoring devices.

As an example, the hypersaturation conditions can be monitored using pulse oximetry according to the present disclosure. Specifically, pulse oximetry can be used to determine a dissolved oxygen index in addition to $SpO_2$. The index is a dimensionless and continuous parameter configured to provide information about a patient's reserve of oxygen dissolved in the blood stream. This index can provide an indication of the patient's oxygenation in the moderate hyperoxic range. The index can assist a user, such as a medical practitioner in exercising her judgment in ensuring that the patient's blood is not overly hypersaturated with oxygen.

The index can be determined because the balance between oxygen supply and demand can alter venous oxygen saturation. As oxygen supply rises, venous oxygen saturation also increases if the patient's oxygen consumption is stable. During situations in which the $SpO_2$ level is at substantially 100%, the patient's oxygen consumption is stable if hemoglobin count and cardiac output are stable. The patient's oxygen consumption is substantially stable during anesthesia, surgery and some other procedures where the patient's oxygen state needs to be monitored. Change in venous oxygen saturation can result in changes in background light absorption at the plurality of wavelengths emitted by an optical sensor of a pulse oximeter in the presence of hyperoxia. Examples of the plurality of emitted wavelengths can include red and infrared wavelengths. The ratios of light absorption at the plurality of emitted wavelengths can be mapped at varying degrees of hyperoxia to allow calculation of the index based on $SvO_2$, which is the patient's oxygen saturation in the venous blood. Changes in $SvO_2$ can be observed when the patient is in moderate hyperoxia as defined herein and can be used to determine the index.

Figure 4:
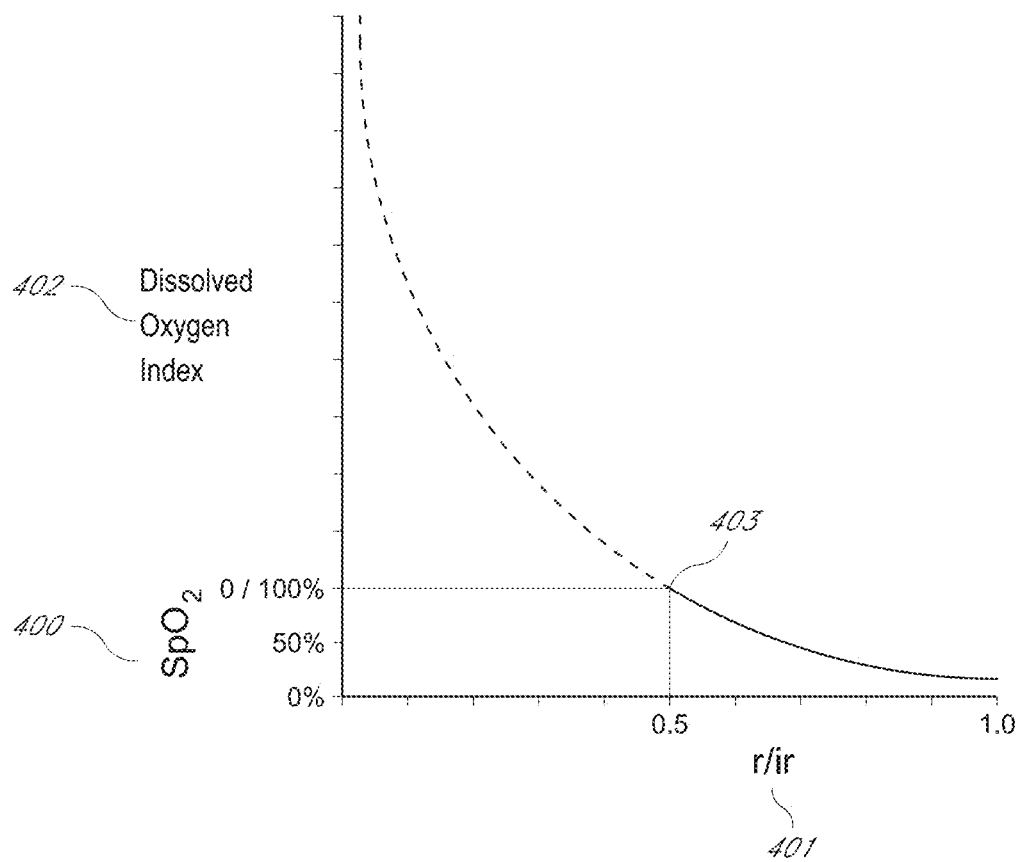
FIG. 4 illustrates an example graph of $SpO_2$ and a patient's hypersaturation indication versus the R/IR ratio.

FIG. 4 illustrates an example graph of $SpO_2$ 400 and the index 402 versus the red to infrared (R/IR) ratio 401. In the illustrated example, the R/IR ratio 401 is at about 0.5 when the $SpO_2$ level 400 is at about 100%. Although the $SpO_2$ level 400 maxes out at 100% saturation, the R/IR ratio 401 continues to decrease when more oxygen is dissolved in the blood. The index 402 can be determined based on the R/IR ratio after the point 403, where the R/IR ratio translates to a $SpO_2$ level of 100% saturation. The index can also be determined when the $SpO_2$ level is slightly below 100% saturation. For example, the index can be determined when the $SpO_2$ level exceeds about 95%, about 97%, or about 98%.

FIGS. 5A-5F and 6A-6F illustrates example displays or a portion thereof having a user-interface for displaying indications of a patient's oxygen state. The displays 500, 600 can be the display 108, 208 of FIGS. 1A and 1, the display 304 of FIG. 2A and 2B, or any other display for displaying physiological parameters. The indications displayed can include $SpO_2$, the index, and/or an increasing or decreasing trend of the index. $SpO_2$ can be displayed as a numerical value 502, 602 and/or a graph 504, 604 with time as the horizontal axis.

As shown in FIGS. 5A-5F, the index can be displayed as a plurality of bars 508 and/or a graph 510 with time as the x-axis. The $SpO_2$ graph 504 and/or the index graph 510 can be plotted along the same horizontal axis. For example, the $SpO_2$ graph 504 can be plotted below the horizontal axis and the index graph 510 can be plotted above the horizontal axis, as shown in the illustrated example. The graphs 504 and 510 can also be superposed on each other or the graph 504 can be above the horizontal axis and the graph 510 can be below the horizontal axis. Using the same horizontal axis can reduce a display area needed for displaying both graphs 504 and 510, and/or allow direct comparison of the $SpO_2$ and index graphs 504, 510.

Figure 5A:
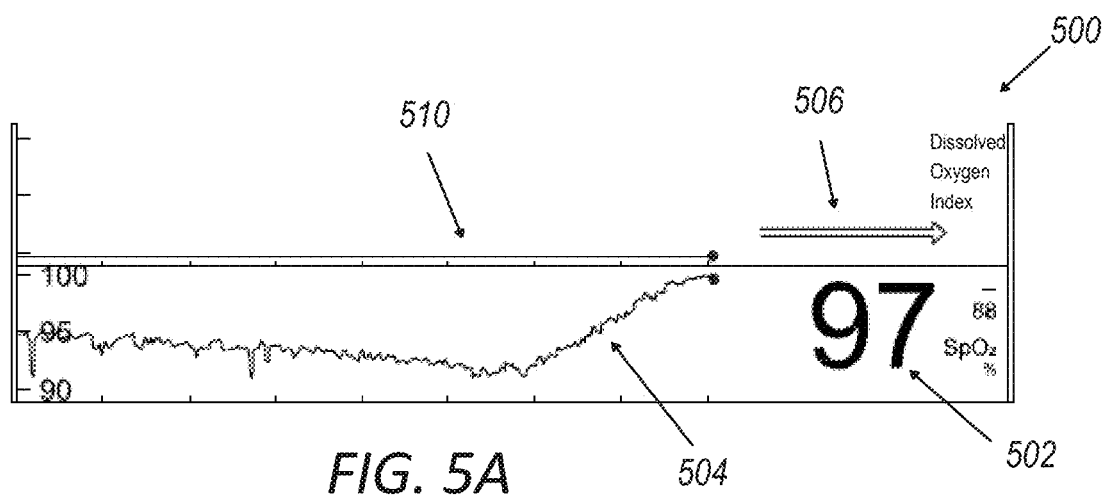
FIGS. 5A-5F illustrate example display screens or portion thereof with graphic user interface for displaying indications of various oxygen states.

The plurality of bars 508 can be stacked generally horizontally, vertically or at any other angle. As shown in FIGS. 5A and 5F, the display 500 does not show any bars when $SpO_2$ is below a threshold level. The threshold level can be about 97%, about 98%, or any other level. The threshold level can vary depending on ambient condition and/or patients. The index graph 510 can be a substantially flat baseline in FIGS. 5A and 5F.

Figure 5B:
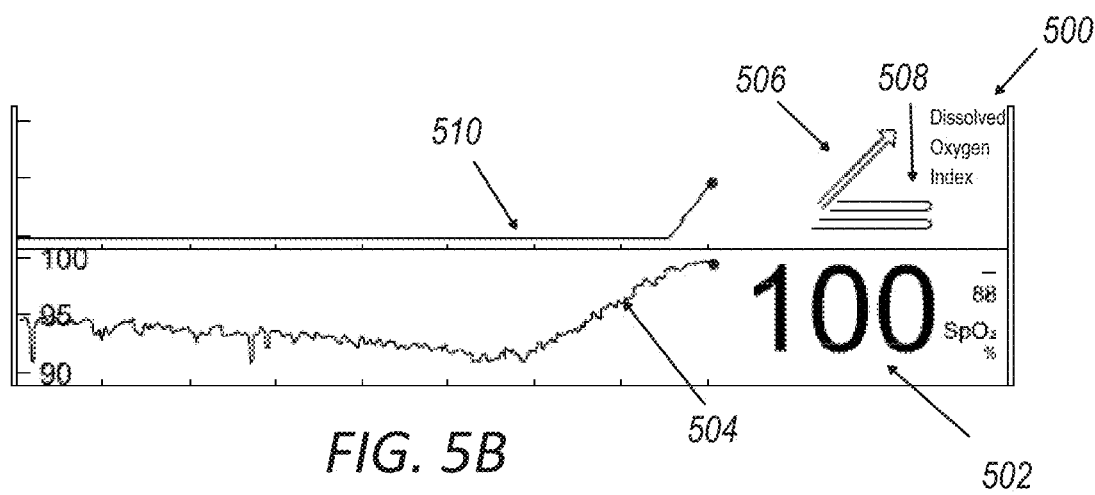
Figure 5C:
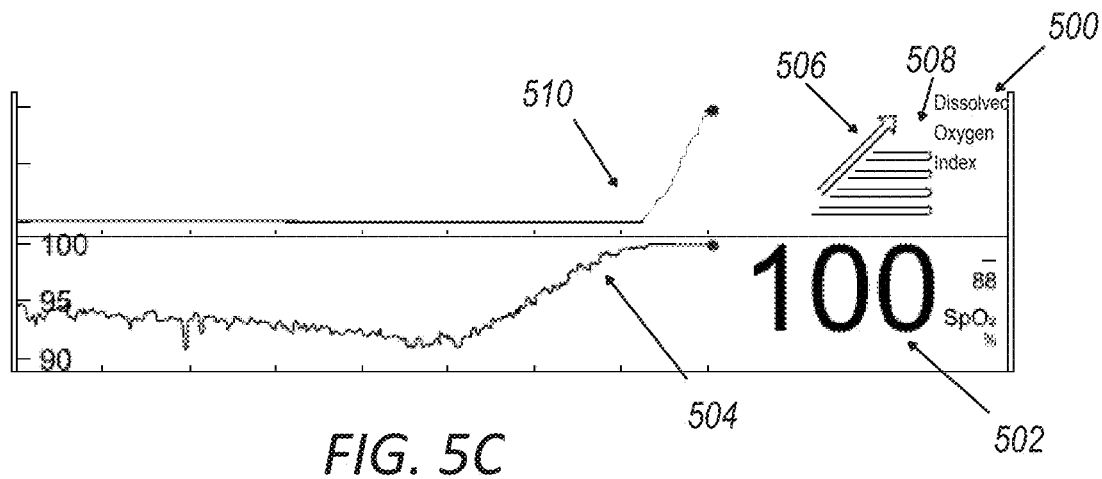
Figure 5D:
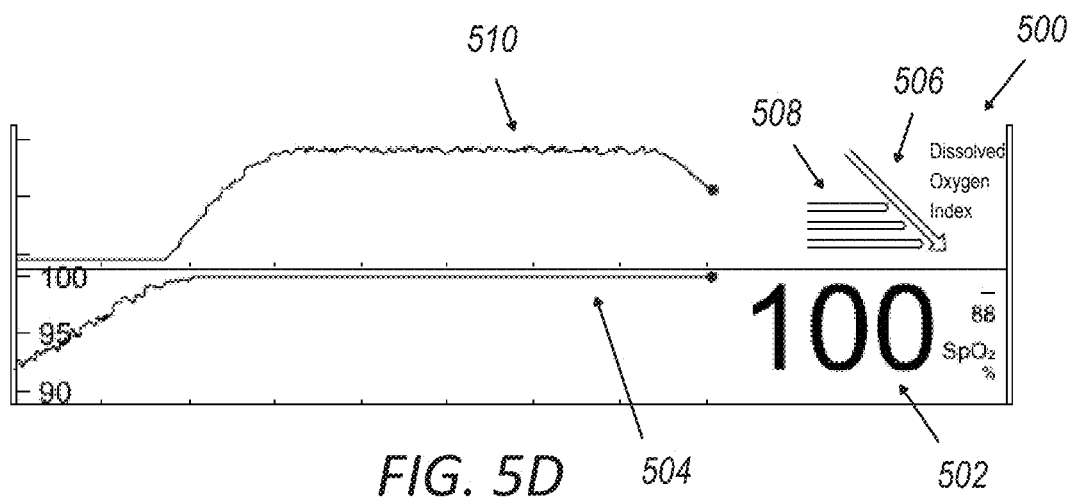
Figure 5E:
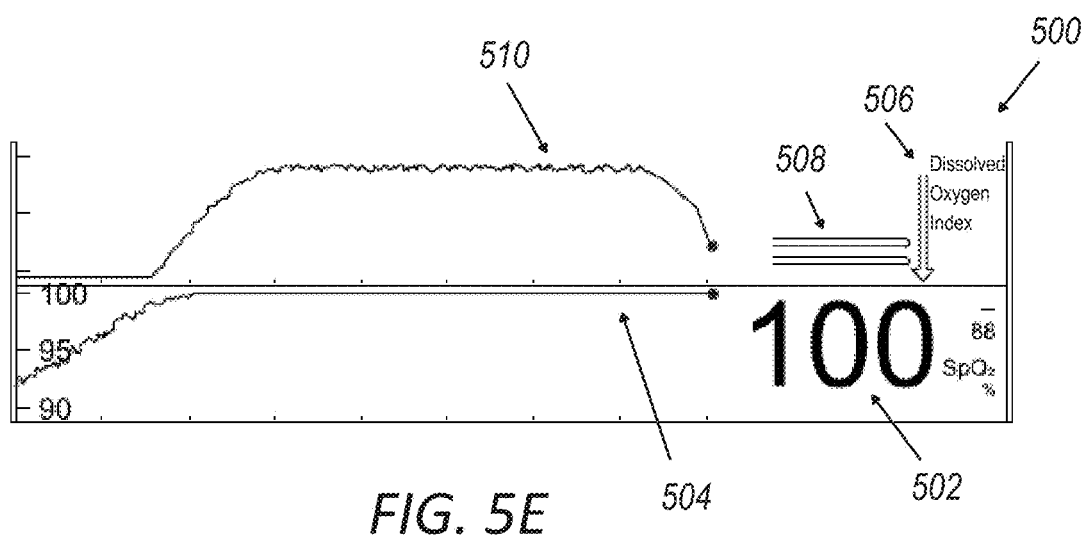
Figure 5F:
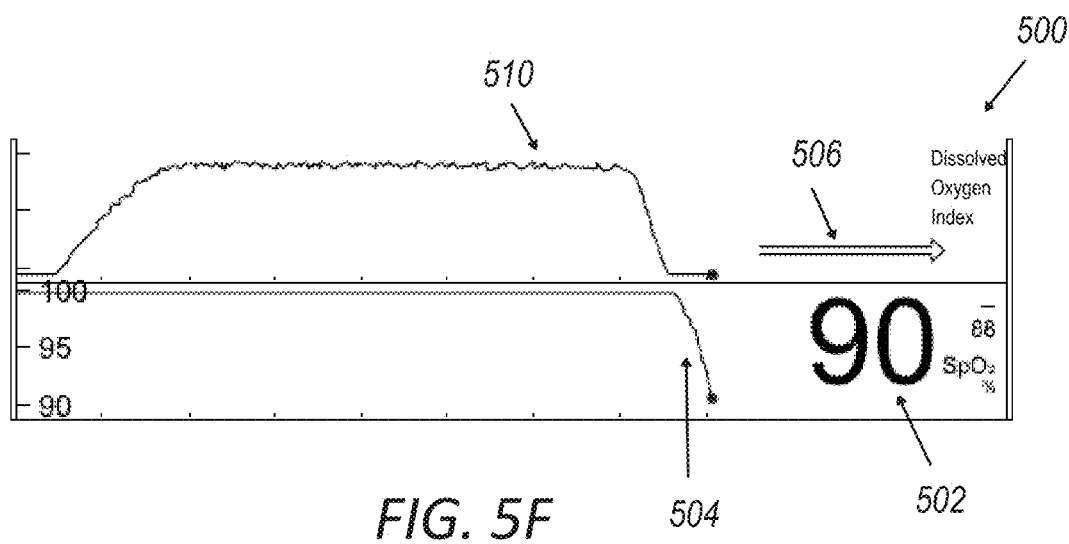

As shown in FIGS. 5B to 5E, $SpO_2$ is above the threshold level and a plurality of rectangular bars 508 are displayed. The number of bars 508 can correspond to an instantaneous index level as shown by a dot in the index graph 510 and can inform the user of the patient's current oxygen reserve. The displays 500 in FIGS. 5B and 5E show two bars. The display 500 in FIG. 5D shows three bars. The display 500 in FIG. 5C shows four bars. Accordingly, the instant index level can be the highest in FIG. 5C and the lowest in FIGS. 5B and 5E. Four bars can be the maximum number of bars so that the index level is at the maximum in FIG. 5C, although other number of bars can be displayed to indicate the maximum index level. The plurality of bars 508 can have the same or different colors. The plurality of bars 508 can also optionally have the same or different shapes and/or sizes. For example, the display 500 can show a plurality of circles, triangles, diamonds, or any other shapes.

The increasing or decreasing trend of the index can be displayed as an arrow 506. The trend of the index can represent the instantaneous gradient of the graph 510. The arrow 506 can be pointing at an angle. The direction of the arrow can correspond to the increasing or decreasing trend of the patient's index. As shown in FIGS. 5A and 5F, when no index bar is shown and/or when the index graph 510 is a substantially flat baseline, the arrow 506 can be pointing generally horizontally. In FIGS. 5B and 5C, when the index is increasing as shown by the slope of the index graph 510, the arrow 506 can be pointing generally upward. In FIGS. 5D and 5E, when the index is decreasing as shown by the slope of the index graph 510, the arrow 506 can be pointing generally downward. The generally upwardly pointing arrow 506 can be on the left hand side of the plurality of bars 508. The generally downwardly pointing arrow 506 can be on the right hand side of the plurality of bars 508. Alternatively, the arrow 506 can always be displayed in the same location relative to the plurality of bars 508, such as on the left, right hand side, on the top, or below the plurality of bars 508.

A magnitude of the angle at which the arrow 506 points can correspond to a rate of increase or decrease of the patient's index. In FIGS. 5B, 5C, and 5D, the index level is increasing or decreasing at a lower rate than the increase or decrease of the index level in FIG. 5E, respectively, as shown by the slope of the corresponding index graph 510. Accordingly, the arrow 506 in FIG. 5E is steeper than the arrow 506 in FIGS. 5B, 5C, and 5D. The rate of increase or decrease of the patient's index can be useful. For example, a clinician to estimate the amount of time before the patient returns from a hypersaturated state to a baseline saturation state based on how quickly the index changes.

As further shown in FIGS. 5B to 5E, the plurality of bars 508 can have incrementally greater lengths. The varying lengths of the plurality of bars 508 can accommodate the arrow 506 at the angle. When the angle of the arrow 506 is small, the increments in the lengths of the plurality of bars 508 can be big. When the angle of the arrow 506 is larger, the increments in the lengths of the plurality of bars 508 can be smaller. The varying lengths of the plurality of bars 508 can allow the display of the plurality of bars 508 and the arrow 506 to be more compact, thereby reducing a display area required for the plurality of bars 508 and the arrow 506. The varying lengths of the plurality of bars 508 can also provide visual indication of the rate of increase or decrease of index. For example, when the plurality of bars 508 are shown as having substantially the same length, the index level can be rapidly increasing or decreasing.

Turning to FIGS. 6A to 6F, the index can be displayed as a circle 608 and/or a graph 610 with time as the horizontal axis. The SpO$_2$ graph 604 and the index graph 610 can be plotted along the same horizontal axis. For example, the SpO$_2$ graph 604 can be plotted below the horizontal axis and the index graph 610 can be plotted above the horizontal axis, as shown in the illustrated example. The graphs 604 and 610 can also be superposed on each other or the graph 604 can be above the horizontal axis and the graph 610 can be below the horizontal axis. Using the same horizontal axis can reduce a display area for displaying both graphs 604 and 610, and/or allow direct comparison of the SpO$_2$ and the index graphs 604, 610. The SpO$_2$ and index graphs 504, 604, 510, 610 can be optional, such as when the display area of a patient monitoring device is too small and/or crowded, or when a user selects a display mode in which the graphs are hidden.

Figure 6A:
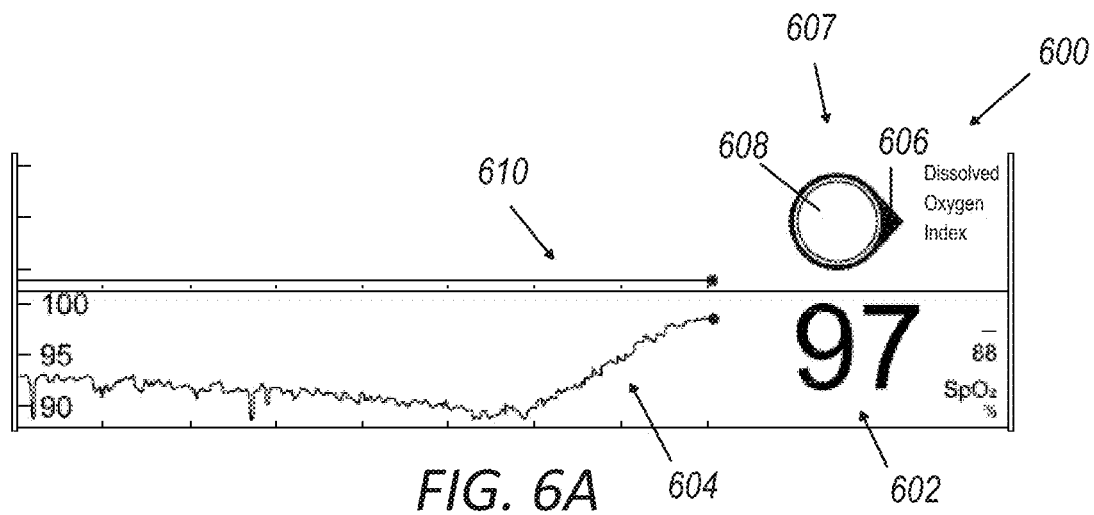
FIGS. 6A-6F illustrate additional example display screens or portion thereof with graphic user interface for displaying indications of various oxygen states.

The circle 608 can be empty, partially filled, or fully filled. The circle can also be a triangle, a rectangle, a diamond, or any other shape. As shown in FIGS. 6A and 6F, the circle 608 is substantially empty when SpO$_2$ is below a threshold level. The threshold level can be about 97%, about 98% or any other suitable level. The graph 610 can be a substantially flat baseline in FIGS. 6A and 6F.

Figure 6B:
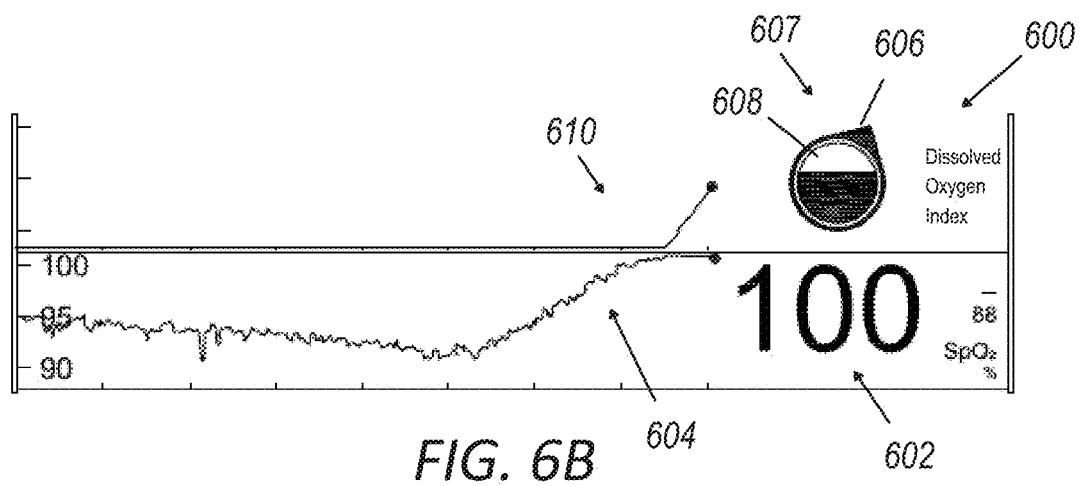
Figure 6C:
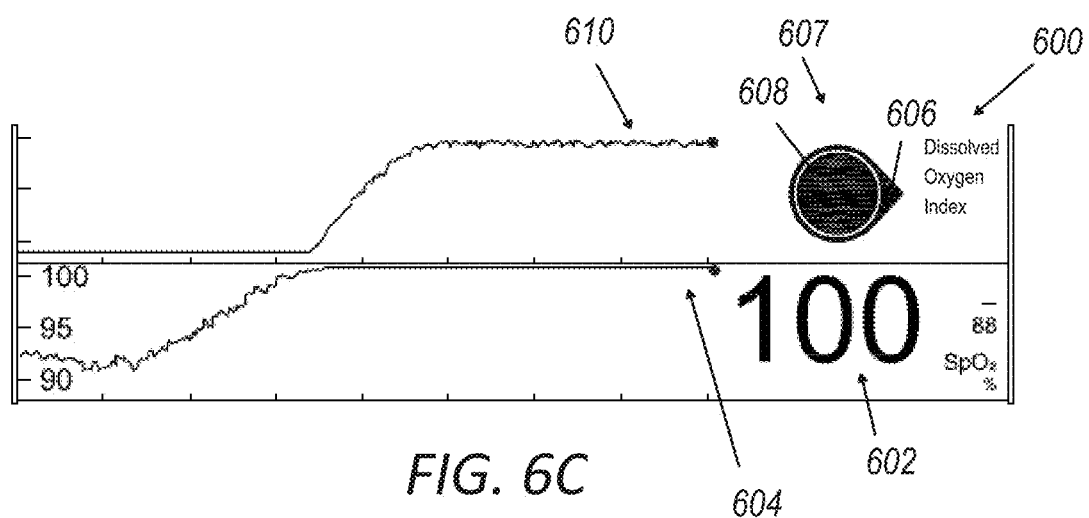
Figure 6D:
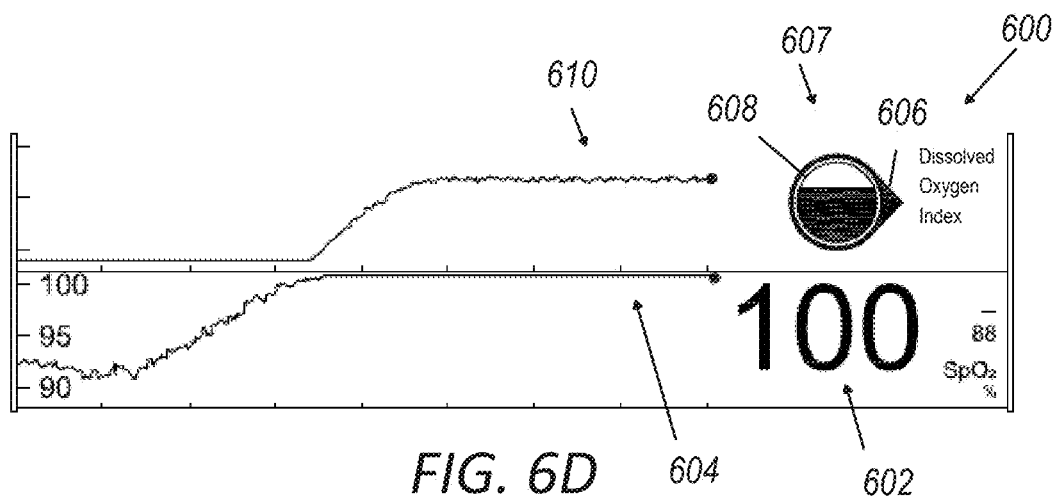
Figure 6E:
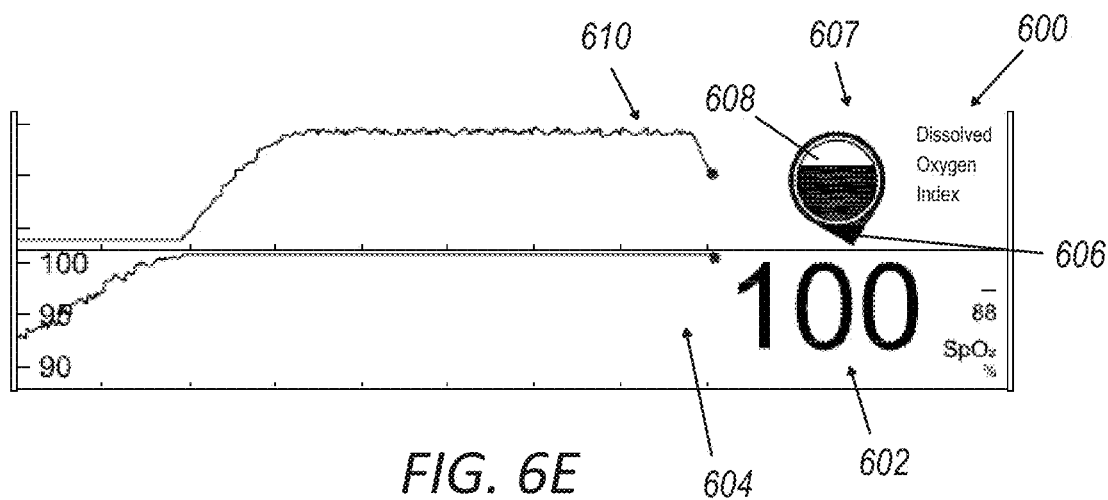
Figure 6F:
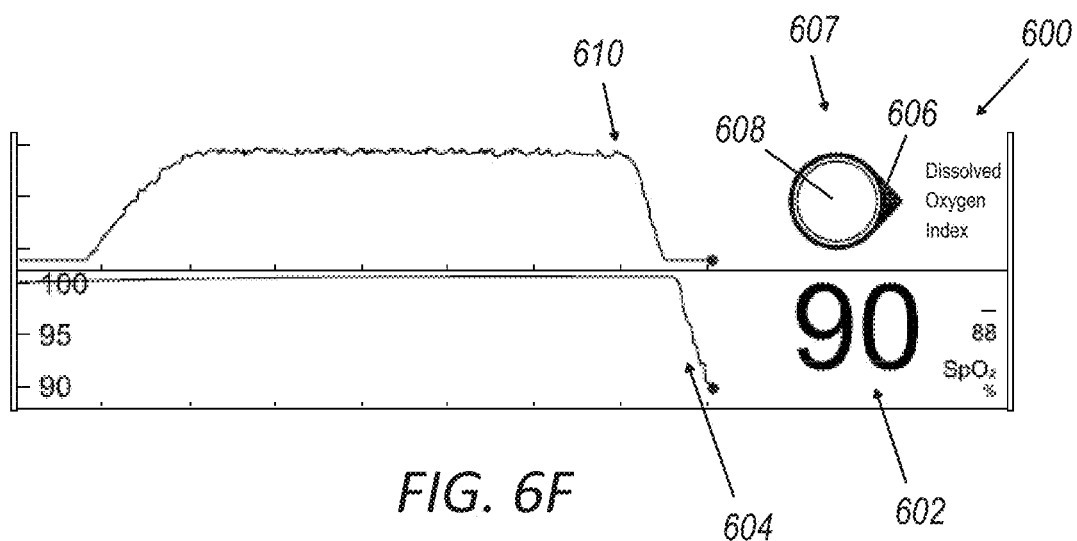

As shown in FIGS. 6B to 6E, SpO$_2$ is above the threshold level and the circle 608 is at least partially filled. The amount or extent of filling of the circle 608 can correspond to an instantaneous index level as shown by a dot in the index graph 610 and can inform the user of the patient's current oxygen reserve. FIGS. 6B, 6D, and 6E show the circle 608 as partially filled. The circles 608 in FIGS. 6D and 6E are slightly more fully filled than the circle 608 in FIG. 6B. FIG. 6C shows the circle 608 as substantially fully filled. Accordingly, the instant index level can be the highest in FIG. 6C and the lowest in FIG. 6B. When the circle 608 is substantially fully filled, the patient's oxygen state may have exceeded mild hyperoxia as defined herein and may be in more severe hyperoxia.

The increasing or decreasing trend of index can be displayed as a pointer 606. The trend of index can be the instantaneous gradient of the index graph 610. The pointer 606 can be pointing at an angle. The direction of the pointer 606 can correspond to the increasing or decreasing trend of the patient's index. As shown in FIGS. 6A and 6F, when the circle 608 is substantially empty and/or when the index graph 610 is a substantially flat baseline, the pointer 606 can be pointing generally horizontally. In FIGS. 6B and 6C, when index is increasing as shown by the slope of the index graph 610, the pointer 606 can be pointing generally upward. In FIGS. 6D and 6E, when index is decreasing as shown by the slope of the graph 610, the pointer 606 can be pointing generally downward.

In FIGS. 6A to 6F, the pointer 606 can be located along the perimeter of the circle 608. A dial 607 can be formed by the circle 608 and the pointer 606. A radial or clock position of the pointer 606 can correspond to an increasing or decreasing trend of the index and/or a rate of the increase or decrease. In FIGS. 6A, 6C, 6D, and 6F, where index is leveling off as indicated by the substantially flat line of the index graph 610, the pointer 606 is at about the three o'clock. In FIG. 6B, where the index level is increasing as indicated by an upward slope of the index graph 610, the pointer 606 is at about the one o'clock. In FIG. 6E, where the index level is decreasing rapidly as indicted by the steep downward slope of the index graph 610, the pointer 606 is at between about five o'clock and about six o'clock.

The displayed indications of SpO$_2$, the index, and/or an increasing or decreasing trend of index on the same display can provide direct visual information of the patient's oxygen state or other physiological parameters. The visual information can be easy to understand by a user upon glancing at the display and/or can reduce the need for the user to further mentally process the oxygen state indications.

In FIGS. 5A and 6A, the patient's index is not displayed when the patient's SpO$_2$ is below a threshold. The threshold can be about 97%, about 98%, or any other suitable level. The threshold can be adjusted based on the patient, the medical procedure being performed, and/or ambient conditions. A user viewing the display 500, 600 in FIGS. 5A and 6A can interpret the readings to indicate that the patient is in a normoxic state. A user of the patient monitoring system, such as a clinician, can safely provide supplemental oxygen, or continue to provide supplemental oxygen, to the patient monitored by the system.

In FIGS. 5B and 6B, the patient's SpO$_2$ is at its maximum. The patient's index is at a moderate level and is increasing. The user viewing the display 500, 600 in FIGS. 5B and 6B can interpret the readings to indicate that patient is in mild hyperoxia as defined herein. The user may reduce, slow down, or stop supplemental oxygen delivery to the patient.

In FIG. 5C, the patient's SpO$_2$ is at its maximum. The patient's index is also at its maximum and is still increasing. The user viewing the display 500 in FIG. 5C can interpret the readings to mean that patient is in more severe hyperoxia. The user may need to stop oxygen delivery to the patient immediately. The user may also consider additional interventional procedures to stop or mitigate damages to the patient caused by the more severe hyperoxia.

In FIG. 6C, the patient's SpO$_2$ and the index are still at their maximum. However, the patient's index has stopped increasing and has leveled off. In some implementations, the leveling of index can be caused by the user cutting off supplemental oxygen delivery to the patient.

In FIG. 5D, the patient's SpO$_2$ is still at its maximum. However, the patient's index is no longer at its maximum and is decreasing. The patient is back in the mild hyperoxic state as defined herein. This can be cause by reduced or cutting off of supplemental oxygen delivery. The user may consider resuming supplemental oxygen delivery.

In FIG. 6D, the patient's $SpO_2$ is still at its maximum. The patient's index is no longer at its maximum, and is neither increasing nor decreasing. This can be an oxygen state that the user wants to maintain for the patient, such as an adult patient.

In FIGS. 5E and 6E, although the patient's $SpO_2$ is still at its maximum, the patient's index is no longer at its maximum and is rapidly decreasing. This can be warning of impending hypoxia. As described above, $SpO_2$ alone may be inadequate and/or lack sufficient sensitivity in providing warning of impending hypoxia. The user may need to resume supplemental oxygen delivery or increase the amount of oxygen delivery to the patient.

In FIGS. 5F and 6F, the patient is $SpO_2$ is below an optimal oxygen saturation level and the patient's index is not displayed. The patient can be in hypoxia. The user must resume supplemental oxygen delivery or increase the amount of oxygen delivery to the patient. The user may also need to consider additional interventional procedures to stop or mitigate damages to the patient due to hypoxia.

The displays as shown in FIGS. 5A-5F and 6A-6F can save time needed for and/or improve accuracy in deciding the amount of supplemental oxygen that needs to be delivered to the patient. The patient's safety during the medical procedure can be improved due to better management of supplemental oxygen delivery. Certain damages, including irreversible damages, to the patient due to hypoxia and/or hyperoxia can be reduced and/or avoided. The improved efficiency and accuracy can be critical for survival of patients, such as patients in the intensive care unit or major invasive surgeries.

Figure 7A:
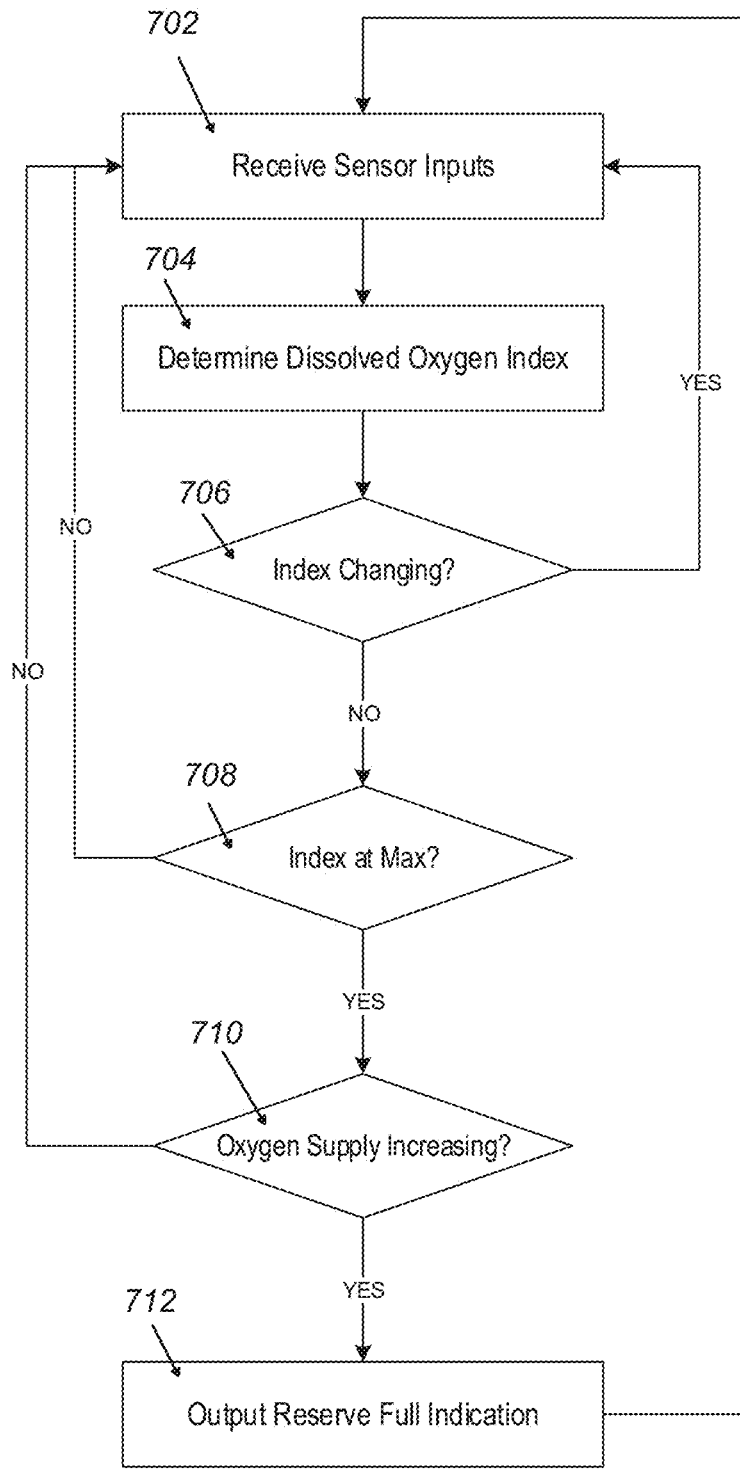
FIG. 7A illustrates an example flow chart for determining a "RESERVE FULL" status of the oxygen states.

In some implementations, the processor of the patient monitoring system can monitor the plateauing of the index. The processor can output alert(s) of the plateauing of the index. As shown in FIG. 7A, at step 702 the processor can receive sensor inputs from the sensor(s) coupled to the system. At step 704, the processor can determine a plurality of physiological parameters based on the sensor input, including but not limited to the dissolved oxygen index, oxygen saturation, or otherwise. At decision step 706, the processor can determine whether the calculated dissolved oxygen index is changing. The processor can determine that the index is changing when fluctuations in the index exceeds a predetermined percentage of the previously calculated index value, such as about 1%, about 2%, about 5%, about 10%, or any ranges between those values, and that the index is not changing when the fluctuations are within the predetermined percentage. The processor can also optionally determine that the index is not changing after the index remains substantially same for a predetermined period of time, such as about 1 second, about 3 seconds, about 5 seconds, about 10 seconds, or any value between those ranges. The delay can allow the processor to ignore temporarily stationary values of the index, which may not be indicative of the physiological state of interest, such as the plateauing of the index. If the index is determined to be changing, the processor can return to step 702 to continue receiving inputs from the coupled sensors. If the index is determined to be not changing, at decision step 708, the processor can determine whether the index is at its maximum value and/or when the index is plateauing at its maximum value. If the index is not changing and not at its maximum value, the processor can return to step 702 to continue receiving inputs from the coupled sensors. If the index is plateauing at its maximum value, at step 710, the processor can determine whether oxygen supply to the patient is increasing. If the oxygen supply to the patient is not increasing (such as when oxygen supply to the patient has been stopped or decreased), the processor can return to step 702 to continue receiving inputs from the coupled sensors. If the oxygen supply to the patient is increasing (for example, if the fraction of oxygen inspired ($FiO_2$) is increasing, the flow rate of oxygen to the patient is increasing, or otherwise), at step 712, the processor can output an indication of the plateauing of the dissolved oxygen index.

Figure 7B:
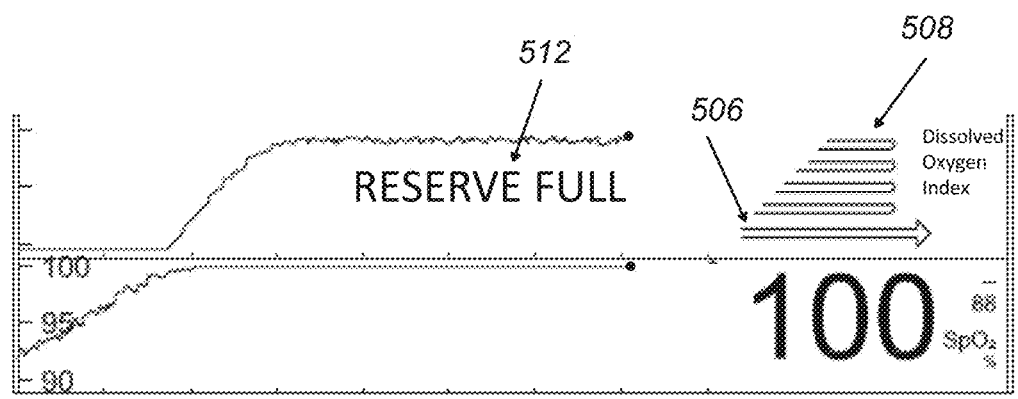
FIGS. 7B and 7C illustrate example display screens or portion thereof with graphic user interface for displaying the "RESERVE FULL" status of the oxygen states.
Figure 7C:
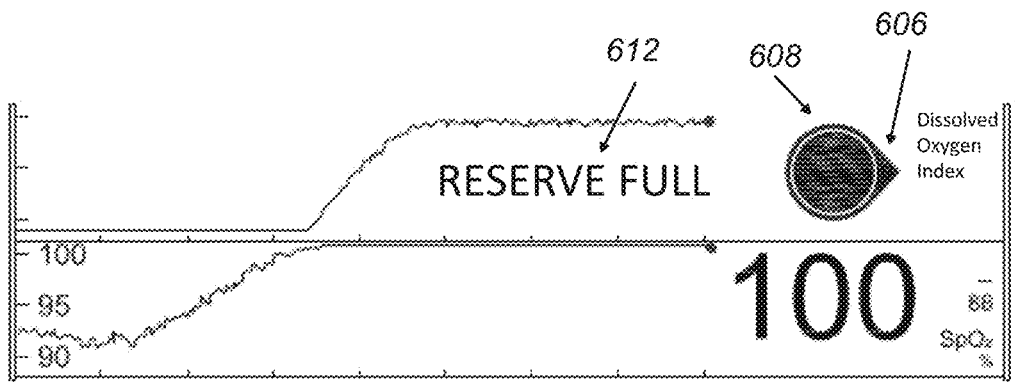

The indication of the plateauing of the dissolved oxygen index can be presented in one or more forms, such as via a visual indicator, text message, and/or audio message. FIGS. 7B and 7C illustrate examples of display of the indication. As shown, a text message of "RESERVE FULL" 512, 612 can be displayed in the display area for the dissolved oxygen index when the index is plateauing and the oxygen supply is still increasing. FIG. 7B also illustrates a maximum number (for example, four, five, or more) of bars 508 and a generally horizontally pointing arrow 506 when the index is plateauing and the oxygen supply is still increasing. FIG. 7C also illustrates the pointer 606 pointing generally horizontally and the circle 608 being substantially full when the index is plateauing and the oxygen supply is still increasing. Additionally or alternatively to the example displays in FIGS. 7B and 7C, the processor can also output an audio message indicating that the index is plateauing when the oxygen supply is increasing.

In one example, the "RESERVE FULL" indication can be used to indicate the completion of a nitrogen washout performed on the patient. The nitrogen washout is a test for estimating a patient's functional residual capacity of the lungs. As the anatomical dead space of the lungs are filled (such as gradually filled) with oxygen after a nitrogen washout, any addition increase in the partial pressure of oxygen, for example, due to a higher $FiO_2$, a higher flow rate of oxygen supply to the patient, or otherwise, can be due to more oxygen getting dissolved in the blood plasma. Accordingly, when the index does not further increase despite an increase in the oxygen supply to the patient, the nitrogen washout is likely complete on the patient. The indication can be in the form of a simple message, a visual alert, an audible alert, a warning message, or any combination of the above.

The display elements disclosed herein, such as the bar(s), arrow, circle, pointer, any of their variants, and any combinations thereof, can represent any physiological parameters, of which the dissolved oxygen index is one example. The display elements disclosed herein can be used to represent a magnitude, an increasing or decreasing trend, and/or a rate of change of any physiological parameter. When the physiological parameter is zero or outside a range that can be calculated by the patient monitoring device, the display area can show a generally horizontally pointing arrow without a bar or its equivalent, or a dial having an empty circle, or its equivalent, pointing at about 3 o'clock. Displaying indications of the magnitude and/or changes of a physiological parameter together can provide more comprehensive information about a patient's physiological conditions in a limited and/or crowded display area than displaying the magnitude and the changes of the physiological parameter separately.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive patient monitoring system for providing an indication of a physiological parameter, the system comprising:
   one or more sensors for outputting signals in response to a patient's physiological conditions;
   one or more signal processors configured to receive the signals and output:

a first indicator indicating a magnitude of a physiological parameter, the first indicator comprising an object of a predetermined shape, and a second indicator indicating an instantaneous trend of the physiological parameter, the second indicator comprising an arrow; and a display responsive to output of the one or more signal processors to display the first and second indicators adjacent to each other, wherein an angle of the arrow corresponds to a rate of change of the physiological parameter, a portion of the first indicator forming a same angle as the arrow such that the portion of the first indicator is parallel to the arrow.

2. The system of claim 1, wherein the first indicator comprises a plurality of the objects of the predetermined shape, a number of the plurality of objects displayed corresponding to the magnitude of the physiological parameter.

3. The system of claim 2, wherein the predetermined shape comprises a rectangle, a circle, a triangle, or a diamond.

4. The system of claim 1, wherein the object is a bar, the first indicator comprising a plurality of stacked bars with varying lengths so as to form a slope, wherein the slope is the portion of the first indicator that is parallel to the arrow.

* * * * *